United States Patent
Zhao et al.

(10) Patent No.: US 10,295,478 B2
(45) Date of Patent: May 21, 2019

(54) MOUNTING PLATE AND OPTICAL INSPECTION APPARATUS

(71) Applicants: BOE TECHNOLOGY GROUP CO., LTD., Beijing (CN); BEIJING BOE DISPLAY TECHNOLOGY CO., LTD., Beijing (CN)

(72) Inventors: Anda Zhao, Beijing (CN); Chunxi Hai, Beijing (CN); Dongyang Feng, Beijing (CN)

(73) Assignees: BOE TECHNOLOGY GROUP CO., LTD., Beijing (CN); BEIJING BOE DISPLAY TECHNOLOGY CO., LTD., Beijing (CN)

( * ) Notice: Subject to any disclaimer, the term of this patent is extended or adjusted under 35 U.S.C. 154(b) by 243 days.

(21) Appl. No.: 15/205,849

(22) Filed: Jul. 8, 2016

(65) Prior Publication Data

US 2017/0191926 A1    Jul. 6, 2017

(30) Foreign Application Priority Data

Jan. 4, 2016 (CN) .......................... 2016 1 0005553

(51) Int. Cl.
*G02B 7/00* (2006.01)
*G01N 21/95* (2006.01)

(52) U.S. Cl.
CPC .............. *G01N 21/95* (2013.01); *G02B 7/00* (2013.01); *G02C 2200/12* (2013.01)

(58) Field of Classification Search
CPC ........ G02B 7/00; G01D 11/30; G01D 11/305; B23C 1/20; A47G 1/08; G03C 21/1619;
(Continued)

(56) References Cited

U.S. PATENT DOCUMENTS 4,304,133 A * 12/1981 Feamster, III ......... B23Q 1/621
                                                        73/633
4,629,171 A    12/1986 Judy et al.
(Continued)

FOREIGN PATENT DOCUMENTS

CN        2900892 Y     5/2007
CN      201654381 U    11/2010
(Continued)

OTHER PUBLICATIONS

Description of MIC-L and MI-90 Girder and Girder Connection, from Hilti website, printed Aug. 31, 2018.*
(Continued)

*Primary Examiner* — Tri T Ton
*Assistant Examiner* — Rebecca C Bryant
(74) *Attorney, Agent, or Firm* — Kinney & Lange, P.A.

(57) ABSTRACT

A mounting plate and an optical inspection apparatus are disclosed. The mounting plate includes: a base plate; at least two first bars disposed above the base plate and extending in a first direction; and at least two second bars extending in a second direction. Each second bar being configured to be slidable in the first direction relative to the at least two first bars. The mounting plate may further comprises a third bar extending in the first direction and disposed between two adjacent first bars, the third bar being configured to be slidable in the second direction relative to the at least two second bars.

20 Claims, 4 Drawing Sheets

(58) Field of Classification Search
CPC .............. G03G 2221/1678–2221/1684; G02C 2200/12–2200/28
See application file for complete search history.

(56) References Cited

U.S. PATENT DOCUMENTS

| | | | |
|---|---|---|---|
| 6,886,659 B2 * | 5/2005 | Simpson | E06C 1/20 182/180.1 |
| 2009/0188197 A1 * | 7/2009 | Irizarry | E04B 9/006 52/655.1 |
| 2017/0259353 A1 * | 9/2017 | Feucht | B23C 1/20 |

FOREIGN PATENT DOCUMENTS

| | | |
|---|---|---|
| CN | 203245762 U | 10/2013 |
| CN | 103639933 A | 3/2014 |
| CN | 104568350 A | 4/2015 |
| CN | 204868596 U | 12/2015 |
| CN | 205262508 U | 5/2016 |

OTHER PUBLICATIONS

First Chinese Office Action, for Chinese Patent Application No. 201610005553.5, dated Jun. 2, 2017, 18 pages.
Second Chinese Office Action, for Chinese Patent Application No. 201610005553.5, dated Oct. 10, 2017, 22 pages.

* cited by examiner

MOUNTING PLATE AND OPTICAL INSPECTION APPARATUS

CROSS-REFERENCE TO RELATED APPLICATION

This application claims benefits of Chinese Patent Application No. 201610005553.5 filed on Jan. 4, 2016 in the State Intellectual Property Office of China, a whole disclosure of which is incorporated herein by reference.

BACKGROUND

Field of the Invention

Embodiments of the invention relate to the field of display technologies, and specially, to a mounting plate and an optical inspection apparatus comprising the mounting plate.

Description of the Related Art

With increase of human cost, recently, Automated Optical Inspection (AOI) apparatuses having an automatic focus function have been widely used to inspect display panels in this field. Before optical inspection, operators need to align and fix the display panels to be inspected on a mounting plate of the AOI apparatus.

In prior art, different mounting plates need to be provided for various display panels of particular specifications and sizes. If specifications and sizes of a display panel to be inspected by the AOI apparatus change, the mounting plate should be correspondingly replaced. Thus, cost for the mounting plates is relative high. Additionally, replacement operation of mounting plates is complicated, resulting in a low efficiency of the optical inspection.

SUMMARY

Embodiments of the invention have been made to overcome or alleviate at least one aspect of the above mentioned disadvantages.

Accordingly, it is an object of the invention to provide a mounting plate and an optical inspection apparatus comprising the mounting plate.

According to one aspect of the invention, there is provided a mounting plate.

In an exemplary embodiment, the mounting plate may comprise: a base plate; at least two first bars disposed above the base plate and extending in a first direction; and at least two second bars extending in a second direction. Each second bar being configured to be slidable in the first direction relative to the at least two first bars.

In a further embodiment, the mounting plate may further comprise a third bar extending in the first direction and disposed between two adjacent first bars, the third bar being configured to be slidable in the second direction relative to the at least two second bars.

In a further embodiment, each second bar may be provided with at least two guiding slots, each first bar being slidably fitted in a corresponding guiding slot.

In a further embodiment, each first bar may have a hollowed structure, and a top of the hollowed structure may be provided with a guiding slit extending in the first direction. Each end of the second bar may be provided with a first locking mechanism, the first locking mechanism may comprise: a pin body passing through the guiding slit into the hollowed structure; a pressing cap connected with a first end of the pin body outside the hollowed structure; a limiting part connected with a second end of the pin body inside the hollowed structure; and a spring fitted around the pin body between the second bar and the pressing cap.

In an alternative embodiment, each of the guiding slots may have a lower limiting wall, a side limiting wall and an upper limiting wall, each end of the second bar may be provided with a second locking mechanism, and the second locking mechanism may comprise: a pin body extending into the guiding slot; a pulling cap connected with a first end of the pin body outside the guiding slot; a limiting part connected with a second end of the pin body inside the guiding slot; and a spring fitted around the pin body between the upper limiting wall of the guiding slot and the limiting part.

In a further embodiment, a portion of each second bar between two adjacent first bars may have an elongate guiding hole, and the third bar is inserted into the elongate guiding hole of each of the at least two second bars.

In a further embodiment, an inner wall of the elongate guiding hole may have an elastic layer, and/or an outer surface of the third bar may have an elastic layer. A width of the elongate guiding hole of the second bar is smaller than a width of the third bar.

In a further embodiment, all the first bars may be identical in structure, all the second bars may be identical in structure, and all the third bars may be identical in structure.

In a further embodiment, at least one of the first bar and the second bar may be provided with scales.

In a further embodiment, the base plate may be provided with a plurality of holes at positions where a display panel to be inspected is to be placed.

According to another aspect of the invention, there is provided an optical inspection apparatus. In an exemplary embodiment, the optical inspection apparatus may comprise the mounting plate according to any of the above embodiments.

BRIEF DESCRIPTION OF THE DRAWINGS

The above and other features of the present invention will become more apparent by describing in detail exemplary embodiments thereof with reference to the accompanying drawings, in which.

DETAILED DESCRIPTION OF PREFERRED EMBODIMENTS

Figure 1:
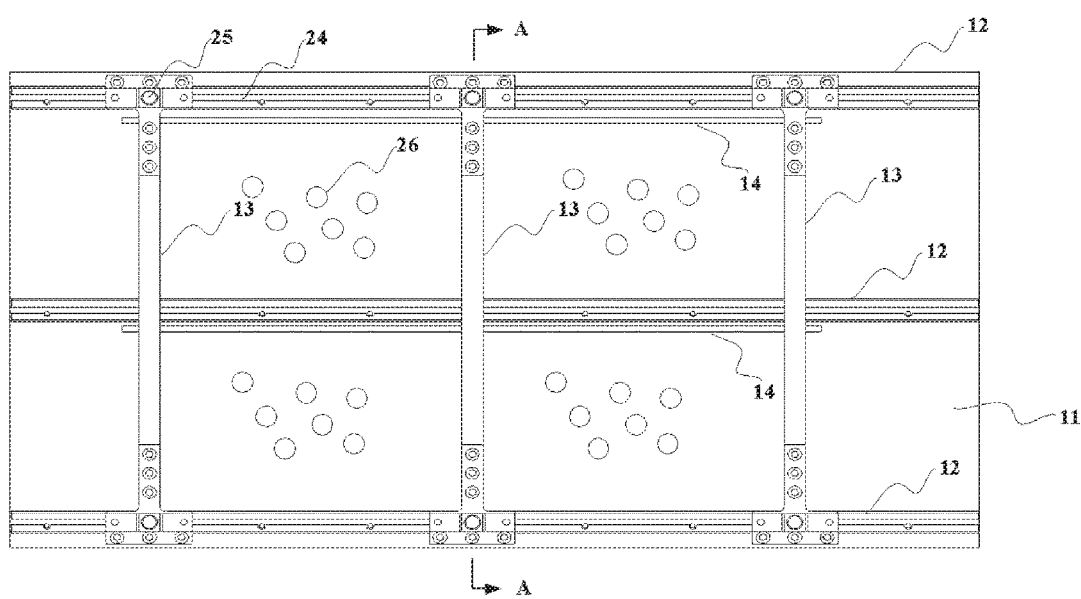
FIG. 1 is an illustrative top view showing a mounting plate according to an embodiment of the invention.

Exemplary embodiments of the present disclosure will be described hereinafter in detail with reference to the attached drawings, wherein the like reference numerals refer to the like elements. The present disclosure may, however, be embodied in many different forms and should not be construed as being limited to the embodiment set forth herein; rather, these embodiments are provided so that the present disclosure will be thorough and complete, and will fully convey the concept of the disclosure to those skilled in the art.

In one aspect of the invention, there is provided a mounting plate. The mounting plate may be used in an optical inspection apparatus, and especially, in an automated optical inspection (AOI) apparatus having an automatic focus function. In an exemplary embodiment, as shown in FIG. 1, the mounting plate includes: a base plate 11; at least two first bars 12 disposed above the base plate 11 and extending in a first direction; and at least two second bars 13 extending in a second direction. Each second bar 13 is configured to be slidable in the first direction relative to the at least two first bars 12.

In a further embodiment, the second bar 13 may be locked to the first bar 12 by a first locking mechanism.

When the second bar 13 is not locked to the first bar 12, it may slide relative to the first bar 12 in the first direction to adjust sizes of a limiting frame formed by two second bars 13 and two first bars 12. For example, a size of the limiting frame in the first direction may be adjusted, as shown in FIG. 1.

In a further embodiment, a third bar 14 extending in the first direction may be disposed between two adjacent first bars 12. The third bar 14 is configured to be slidable in the second direction relative to the at least two second bars 13. Additionally, in a still further embodiment, the third bar 14 may be locked to the second bar 13 by a second locking mechanism.

In an exemplary embodiment, the first direction may be perpendicular to the second direction.

With the mounting plate according to the embodiment of the invention, a limiting frame may be formed by the first bar(s) 12, the second bar(s) 13 and the third bar 14. Moreover, through moving the second bar(s) 13 in the first direction and moving the third bar 14 in the second direction, sizes of the limiting frame in the first and/or the second directions may be adjusted. When these bars are adjusted to suitable positions, they can be locked with each other by the first and/or the second locking mechanisms, so that the sizes of the limiting frame can be fixed. Therefore, the mounting plate according to the embodiment of the invention may be used for optical inspection of various display panels having different sizes. As compared with prior arts, the mounting plate needs not to be replaced even if sizes of a display panel to be inspected changes, thus, cost for the mounting plate is reduced, and efficiency of optical inspection is increased.

The numbers of the first bars 12 and the second bars 13 may be more than two, and the number of the third bars 4 may be determined based on the number of the first bars 12. For example, when there are two first bars 12 and two second bars 13, the number of the third bar 14 is one, and in this condition, the mounting plate may form one limiting frame having adjustable sizes, which may be used to fix one display panel. In the embodiment shown in FIG. 1, there are three first bars 12, three second bars 13 and two third bars 14, and in this condition, the mounting plate may form four limiting frames having adjustable sizes, which may fix four display panels. The optical inspection apparatus may perform optical inspection for several display panels in one time, and thereby efficiency of the inspection is increased.

The second bars 13 may be slidably connected to the at least two first bars 12 in various different manners. For example, in an embodiment shown in FIG. 2, each second bar 13 may be provided with at least two guiding slots 15, each first bar 12 is slidably fitted in a corresponding guiding slot 15. In an alternative embodiment that is not shown, the guiding slots 15 in the second bars 13 may be replaced by guiding holes. When a second bar 13 is to be assembled to the first bars 12, the first bars 12 may be fit into the guiding slots 15 or guiding holes of the second bars 13, then the second bar 13 is moved along the first bars 12 to a suitable position and locked in that position. The third bar 14 may be assembled to the second bars 13 in a similar way.

The first locking mechanism and the second mechanism may be embodied by any known locking mechanism in this field. In the exemplary embodiments shown in FIGS. 1 to 4, each first bar 14 may have a hollowed structure and have a guiding slit 24 located at its top and extending in the first direction. Each second bar 13 is provided with two locking mechanisms at two ends thereof respectively, and each of the locking mechanisms may include: a pin body 191 passing through the guiding slit 24 into the hollowed structure; a pressing cap 25 connected with a first end of the pin body 191 outside the hollowed structure; a limiting part 211 connected with a second end of the pin body 191 inside the hollowed structure; and a spring 221 disposed surrounding the pin body 191 and between the second bar 13 and the pressing cap 25.

Figure 4:
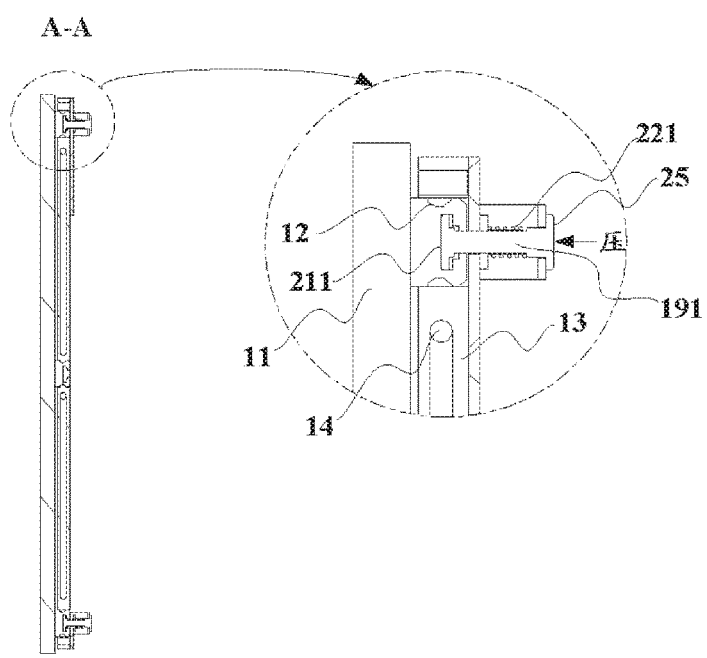
FIG. 4 is an illustrative cross-sectional view of the mounting plate taken along line A-A of FIG. 1.

The spring 221 is pre-compressed, and under a spring force from the spring, the limiting part 211 abuts against a top wall of the hollow structure so as to realize locking between the second bar 13 and the first bar 12. When the pressing cap 25 is pressed down (the pressing cap 25 is in a pressed-down state as shown in FIG. 4), the limiting part 211 is disengaged from the top wall of the hollow structure, such that the second bar 13 may slide relative to the first bar 12. With such a configuration, locking and unlocking between the second bar 13 and the first bar 12 may be achieved.

Figure 5:
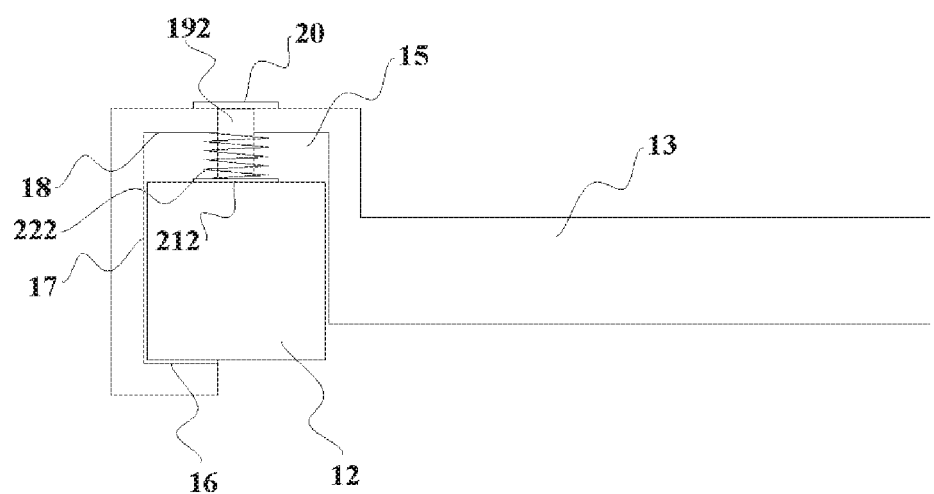
FIG. 5 is an illustrative view showing a locking mechanism between a first bar and a second bar according to another embodiment of the invention.

According to another embodiment, as shown in FIG. 5, each of the guiding slots at two ends of the second bar 13 includes a lower limiting wall 16, a side limiting wall 17 and an upper limiting wall 18. Each of two ends of the second bar 13 is provided with a locking mechanism, which may include: a pin body 192 extending into the guiding slot 15; a pulling cap 20 connected with a first end of the pin body 192 outside the guiding slot 15; a limiting part 212 connected with a second end of the pin body 192 inside the guiding slot 15; and a spring 222 fitted around the pin body 192 and between the upper limiting wall 18 of the guiding slot 15 and the limiting part 212.

The spring 222 is pre-compressed, and under a spring force from the spring, the limiting part 212 abuts against the first bar 12 so as to realize locking between the second bar 13 and the first bar 12. When the pulling cap 20 is pulled upwards, the limiting part 212 is disengaged from the first bar 12, such that the second bar 13 may slide relative to the first bar 12. With such a configuration, locking and unlocking between the second bar 13 and the first bar 12 may be achieved. In the embodiment shown in FIG. 5, the pin body 192 passes through the upper limiting wall 18 of the guiding slot 15. However, in an alternative embodiment that is not shown, the pin body may be configured to pass through the side limiting wall 17.

The third bar 14 may be slidably connected to the second bar 13 in a similar manner.

Figure 2:
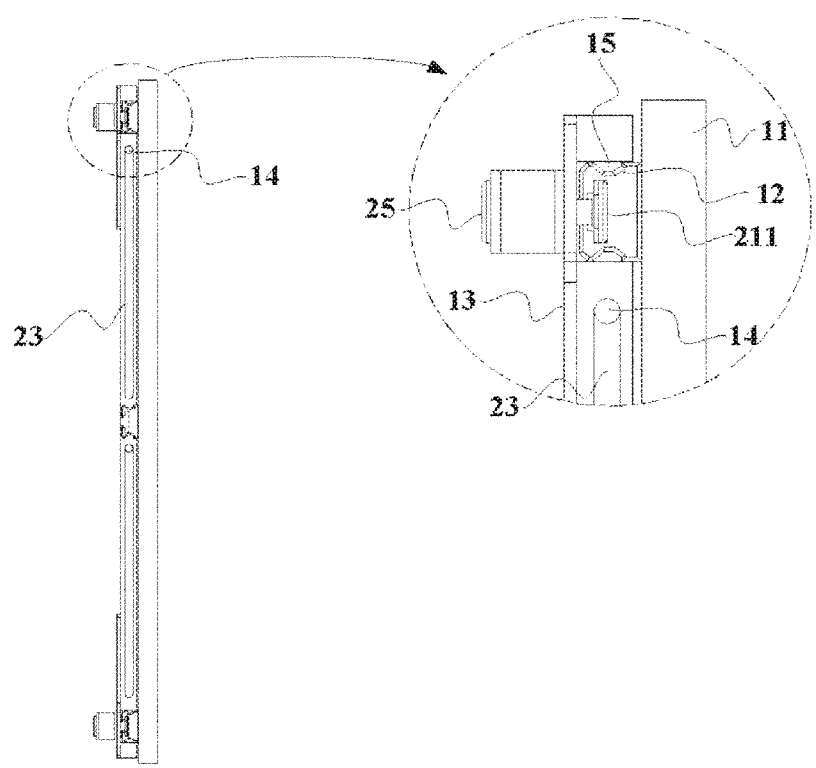
FIG. 2 is an illustrative right view showing a mounting plate according to an embodiment of the invention.
Figure 3:
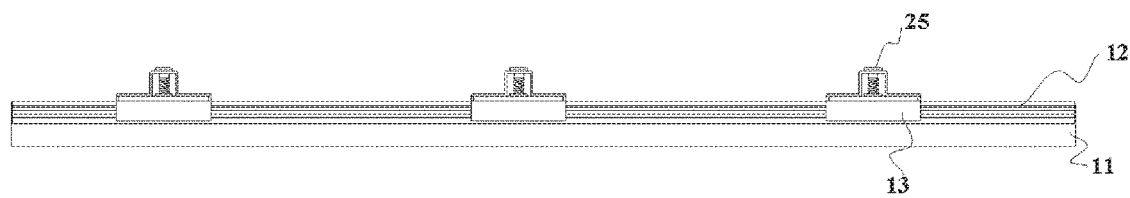
FIG. 3 is an illustrative front view showing a mounting plate according to an embodiment of the invention.

In the exemplary embodiments, as shown in FIGS. 1 and 2, a portion of the second bar 13 located between two adjacent first bars 12 has an elongate guiding hole 23, and each third bar 14 is slidably mounted in the guiding holes 23 of the at least two second bars 13. Such a configuration is simple and has a low production cost, and the third bar 14 is not prone to disengage from the second bar 13, such that the configuration is reliable.

In a preferred embodiment of the invention, an inner wall of the elongate guiding hole 23 of the second bar 13 may have an elastic layer, and/or an outer surface of the third bar 14 may have an elastic layer, and a width of the elongate guiding hole 23 of the second bar 13 is smaller than a width of the third bar 14. In such a manner, when the third bar 14 is inserted into the elongate guiding hole 23 of the second bar 13, the inner wall of the elongate guiding hole 23 of the second bar 13 and/or the outer surface of the third bar 14 may be elastically deformed, and thereby locking a relative position between the second bar 13 and the third bar 14. If a position of the third bar 14 needs to be adjusted, a force may be applied to the third bar 14 to move the third bar 14 relative to the second bar 13. With this design, no additional locking mechanism is needed, such that the structure of the mounting plate can be simplified, and an operation of the mounting plate may be facilitated. Moreover, since the outer surface of the third bar 14 has the elastic layer, damage to the display panel or other components may be reduced.

In a preferred embodiment of the invention, the first bars 12 are identical in structure, the second bars 13 are identical in structure, and the third bars 14 are also identical in structure. The first bars 12 can be arbitrarily interchanged, so do the second bars 13 and the third bars 14, such that assembling of these components may be facilitated and production cost may be reduced.

Optionally, the first bar 12 may be provided with scales, and/or the second bar 13 may be provided with scales. Positions of the second bars 13 and/or the third bars 14 may be adjusted with aid of these scales, such that adjustment operation may be more accurate and convenient. For an AOI apparatus having an automatic focus function, the first bars 12 and the second bars 13 may not be provided with scales.

As shown in FIG. 1, the base plate 11 is provided with a plurality of holes 26. Such holes may decrease a weight of the mounting plate, and wires may pass through the holes. Additionally, the holes may also facilitate lifting up a display panel from below by operators.

When utilizing the mounting plate shown in FIG. 1 to limit and fix a display panel, first, a position of the second bar 13 relative to the first bar 12 is adjusted such that an interval between two adjacent second bars 13 matches a size of the display panel in the first direction; then, a position of the third bar 14 relative to the second bar 13 is adjusted such that an interval between two adjacent third bars 14 matches a size of the display panel in the second direction. In this condition, the display panel is placed into a limiting frame formed by two adjacent second bars 13, the intermediate first bar 12 and a third bar 14, such that the display panel may be limited and fixed in position. Four display panels may be fixed on the mounting plate shown in FIG. 1. After mounting of the display panels, the optical inspection apparatus may focus on the display panels and perform an optical inspection on the display panels.

In another aspect of the invention, there is provided an optical inspection apparatus. In an exemplary embodiment, the optical inspection apparatus may include the mounting plate according to any of the above embodiments. As compared with prior arts, the mounting plate needs not to be replaced even if sizes of a display panel to be inspected change, thus, cost for the mounting plate may be reduced, and efficiency of optical inspection may be increased. The optical inspection apparatus may be an AOI apparatus.

Although several exemplary embodiments have been shown and described, it would be appreciated by those skilled in the art that various changes or modifications may be made in these embodiments without departing from the principles and spirit of the disclosure, the scope of which is defined in the claims and their equivalents.

What is claimed is:

1. A mounting plate, comprising:
a base plate;
at least two first bars disposed above the base plate and extending in a first direction; and
at least two second bars extending in a second direction, each second bar being configured to be slidable in the first direction relative to the at least two first bars and relative to others of the at least two second bars,
wherein each first bar has a hollowed structure, and a top of the hollowed structure is provided with a guiding slit extending in the first direction;
wherein each end of the second bars is provided with a first locking mechanism, the first locking mechanism comprising:
a pin body passing through the guiding slit into the hollowed structure and extending in a third direction perpendicular to both the first direction and the second direction;
a pressing cap connected with a first end of the pin body outside the hollowed structure;
a limiting part connected with a second end of the pin body inside the hollowed structure; and
a spring fitted around the pin body between the second bar and the pressing cap, and
wherein the limiting part is movable in the third direction so that the limiting part is switchable between abutment against the top of the hollowed structure of a respective first bar and disengagement from the top of the hollowed structure of the respective first bar.

2. The mounting plate according to claim 1, further comprising a third bar extending in the first direction and disposed between two adjacent first bars, the third bar being configured to be slidable in the second direction relative to the at least two second bars.

3. The mounting plate according to claim 1, wherein each second bar is provided with at least two guiding slots, each first bar being slidably fitted in at least two guiding slots of the at least two second bars.

4. A mounting plate, comprising:
a base plate;
at least two first bars disposed above the base plate and extending in a first direction; and
at least two second bars extending in a second direction, each second bar being configured to be slidable in a first direction relative to the at least two first bars and relative to others of the at least two second bars,
wherein each second bar is provided with at least two guiding slots, each first bar being slidably fitted in at least two guiding slots of the at least two second bars,
wherein each of the guiding slots has a lower limiting wall, a side limiting wall and an upper limiting wall; and
wherein each end of the second bar is provided with a second locking mechanism, the second locking mechanism comprising:
a pin body extending into the guiding slot in a third direction perpendicular to both the first direction and the second direction;
a pulling cap connected with a first end of the pin body outside the guiding slot;
a limiting part connected with a second end of the pin body inside the guiding slot; and
a spring fitted around the pin body between the upper limiting wall of the guiding slot and the limiting part, and wherein the limiting part is movable in a third direction so that the limiting part is switchable between abutment against the first bar and disengagement from the first bar.

5. The mounting plate according to claim 2, wherein each second bar is provided with at least two guiding slots, each first bar being slidably fitted in at least two guiding slots of the at least two second bars.

6. The mounting plate according to claim 2, wherein a portion of each second bar between two adjacent first bars has an elongate guiding hole, the third bar being slidably fitted into the elongate guiding hole of each of the at least two second bars.

7. The mounting plate according to claim 6, wherein a width of the elongate guiding hole of the second bar is smaller than a width of the third bar, and an inner wall of the elongate guiding hole has an elastic layer, and/or an outer surface of the third bar has an elastic layer, so that the inner wall of the elongate guiding hole and/or the outer surface of the third bar is elastically deformed to slidably fit the third bar into the elongate guiding hole of each of the at least two second bars.

8. The mounting plate according to claim 2, wherein all the first bars are identical in structure, and all the second bars are identical in structure.

9. The mounting plate according to claim 1, wherein at least one of the first bar and the second bar is provided with scales.

10. The mounting plate according to claim 1, wherein the base plate is provided with a plurality of holes at positions where a display panel to be inspected is to be placed.

11. The mounting plate according to claim 2, wherein the base plate is provided with a plurality of holes at positions where a display panel to be inspected is to be placed.

12. An optical inspection apparatus, comprising the mounting plate according to claim 1.

13. An optical inspection apparatus, comprising the mounting plate according to claim 2.

14. The mounting plate according to claim 4, further comprising a third bar extending in the first direction and disposed between two adjacent first bars, the third bar being configured to be slidable in the second direction relative to the at least two second bars.

15. The mounting plate according to claim 14, wherein a portion of each second bar between two adjacent first bars has an elongate guiding hole, the third bar being slidably fitted into the elongate guiding hole of each of the at least two second bars.

16. The mounting plate according to claim 15, wherein a width of the elongate guiding hole of the second bar is smaller than a width of the third bar, and an inner wall of the elongate guiding hole has an elastic layer, and/or an outer surface of the third bar has an elastic layer, so that the inner wall of the elongate guiding hole and/or the outer surface of the third bar is elastically deformed to slidably fit the third bar into the elongate guiding hole of each of the at least two second bars.

17. The mounting plate according to claim 4, wherein at least one of the first bar and the second bar is provided with scales.

18. The mounting plate according to claim 4, wherein the base plate is provided with a plurality of holes at positions where a display panel to be inspected is to be placed.

19. The mounting plate according to claim 4, wherein all the first bars are identical in structure, and all the second bars are identical in structure.

20. An optical inspection apparatus, comprising the mounting plate according to claim 4.

* * * * *